(12) United States Patent
Backman et al.

(10) Patent No.: US 10,241,041 B2
(45) Date of Patent: Mar. 26, 2019

(54) BIOLOGICAL TISSUE ANALYSIS BY INVERSE SPECTROSCOPIC OPTICAL COHERENCE TOMOGRAPHY

(71) Applicant: NORTHWESTERN UNIVERSITY, Evanston, IL (US)

(72) Inventors: Vadim Backman, Chicago, IL (US); Ji Yi, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/590,745

(22) Filed: May 9, 2017

(65) Prior Publication Data

US 2018/0017487 A1    Jan. 18, 2018

Related U.S. Application Data

(63) Continuation of application No. 13/651,196, filed on Oct. 12, 2012, now Pat. No. 9,678,007.

(60) Provisional application No. 61/547,365, filed on Oct. 14, 2011.

(51) Int. Cl.
| | | |
|---|---|---|
| G06K 9/00 | (2006.01) | |
| G01N 21/47 | (2006.01) | |
| A61B 5/00 | (2006.01) | |

(52) U.S. Cl.
CPC ....... *G01N 21/4795* (2013.01); *A61B 5/0066* (2013.01)

(58) Field of Classification Search
CPC ................................ A61B 5/0066; G06K 9/36
See application file for complete search history.

(56) References Cited

U.S. PATENT DOCUMENTS

| | | | | |
|---|---|---|---|---|
| 2003/0028100 | A1* | 2/2003 | Tearney | A61B 1/00165 600/431 |
| 2007/0229801 | A1* | 10/2007 | Tearney | A61B 5/0062 356/73 |
| 2010/0033727 | A1* | 2/2010 | Ko | A61B 3/102 356/451 |
| 2013/0095519 | A1* | 4/2013 | Backman | A61B 5/0066 435/34 |

(Continued)

OTHER PUBLICATIONS

Leitgeb et al. ("Spectral measurement of absorption by spectroscopic frequency-domain optical coherence tomography") (Year: 2000).*

(Continued)

*Primary Examiner* — Avinash Yentrapati
(74) *Attorney, Agent, or Firm* — Hanley, Flight and Zimmerman, LLC

(57) ABSTRACT

A method and system to measure and image the full optical scattering properties by inverse spectroscopic optical coherence tomography (ISOCT) is disclosed. Tissue is modeled as a medium with continuous refractive index (RI) fluctuation and such a fluctuation is described by the RI correlation functions. By measuring optical quantities of tissue (including the scattering power of the OCT spectrum, the reflection albedo α defined as the ratio or scattering coefficient $\mu_s$, and the back-scattering coefficient $\mu_b$), the RI correlation function can be inversely deduced and the full set of optical scattering properties can be obtained.

20 Claims, 15 Drawing Sheets

(56) References Cited

U.S. PATENT DOCUMENTS

2014/0285812 A1* 9/2014 Levitz .................. A61B 5/0066
356/479

OTHER PUBLICATIONS

Kodach et al. ("Determination of the scattering anisotropy with optical coherence tomography") (Year: 2011).*
Ash, E. & Nicholls, G., "Super-resolution aperture scanning microscope," Nature 237:510-512 (1972), 4 pages.
Betzig, E. et al., "Imaging intracellular fluorescent proteins at nanometer resolution," Science 313:1642-1645 (2006), 4 pages.
Caron, H. et al., "The human transcriptome map: Clustering of highly expressed genes in chromosomal domains," Science 291:1289-1292 (2001), 4 pages.
Cremer, M. et al., "Inheritance of gene density related higher order chromatin arrangements in normal and tumor cell nuclei," The Journal of Cell Biology 162:809-820 (2003), 12 pages.
Gao, W., "Quantitatively characterizing fluctuations of dielectric susceptibility of tissue with fourier domain optical aoherence tomography," J. Opt. Soc. Am. A 27:2588-2592 (2010), 5 pages.
Goetze, S. et ai.,"The three-dimensional structure of human interphase chromosomes is related to the transcriplome map," Mol. Cell. Bioi. 27:4475-4487 (2007), 14 pages.
Gustafsson, M.G. L.,"Surpassing the lateral resolution limit by a factor of two using structured illumination microscopy," Journal of Microscopy 198:82-87 (2000), 7 pages.
Hell, S. W. & Wichmann, J., "Breaking the diffraction resolution limit by stimulated emission: stimulated-emission-depletion fluorescence microscopy," Opt. Lett. 19:780-782 (1994), 4 pages.
Ishimaru, A., "Wave Propagation and Scattering in Random Media," (Wiley-IEEE Press, 1999), 9 pages.
Izkan, I. et al., "Confocal light absorption and scattering spectroscopic microscopy monitors organelles in live cells with no exogenous labels," Proc. of the Nail. Acad. of Sci. 104:17255-17260 (2007), 7 pages.
Jacob, Z., Alekseyev, L. V. & Narimanov, E., "Optical hyperlens: Far-field imaging beyond the diffraction limit," Opt. Express 14:8247-8256 (2006), 10 pages.
Joo, C., Akkin, T., Cense, B., Park, B. H. & de Boer, J. F., "Spectral-domain optical coherence phase microscopy for quantitative phase-contrast imaging," Opt. Lett. 30:2131-2133 (2005), 3 pages.
Leitgeb, R. et al., "Spectral measurement of absorption by spectroscopic frequency-domain optical coherence tomography," Opt. Lett. 25:820-822 (2000), 3 pages.
Lewis, A., Isaacson, M., Harootunian, A. & Muray, A., "Development of a 500 spatial resolution light microscope: I. light is efficiently transmitted through [lambda]/16 diameter apertures," Ultramicroscopy 13:227-231 (1984), 6 pages.
Liu, Z. et al., "Far-Field Optical Superlens Imaging," Nano Letters 7:403-408 (2007), 17 pages.
Liu, Z. Lee, H. Xiong, Y., Sun, C. & Zhang, X., "Far-field optical hyperlens magnifying sub-diffraction-limited objects," Science 315:1686, Mar. 27, 2007, 2 page.
Nadiarnykh, 0., LaComb, R., Brewer, M. & Campagnola, P., "Alterations of the extracellular matrix in ovarian cancer studied by second harmonic generation imaging microscopy," BMC Cancer 10:94 (2010), 14 Pages.
Pupa, S., Menard, S., Forti, S. & Tagliabue, E, "New insights into the role of extracellular matrix during tumor onset and progression," Journal of Cellular Physiology 192:259-267 (2002), 9 pages.
Rogers, J.D., Ilker R. Capoglu & Backman, V., "Nonscalar elastic light scattering from continuous random media in the born approximation," Opt. Lett. 34:1891-1893 (2009), 3 pages.
Rust, Michael J., X. Z., Mark Bates, "Sub-diffraction-limit imaging by stochastic optical reconstruction microscopy (storm)," Nat Melh 3:793-796 (2006), 3 pages.
There!, N. et al., "Increased extracellular matrix remodeling is associated with tumor progression in human hepatocellular carcinomas," Hepatology (Baltimore, Md) 34:82-88 (2001), 7 pages.
Wang, Z. et al., "Spatial light interference microscopy (slim)," Opt. Express 19:1016-1026 (2011) 11 pages.
United States Patent and Trademark Office, "Notice of Allowance", issued in connection with U.S. Appl. No. 13/651,196, dated Feb. 9, 2017, 27 pages.
United States Patent and Trademark Office, "Non-Final Office action", issued in connection with U.S. Appl. No. 13/651,196, dated Sep. 23, 2016, 13 pages.
United States Patent and Trademark Office, "Final Office action", issued in connection with U.S. Appl. No. 13/651,196, dated May 19, 2016, 18 pages.
United States Patent and Trademark Office, "Non-Final Office action", issued in connection with U.S. Appl. No. 13/651,196, dated Oct. 5, 2015, 15 pages.
United States Patent and Trademark Office, "Non-Final Office action", issued in connection with U.S. Appl. No. 13/651,196, dated Feb. 13, 2015, 11 pages.
Kodach et al., ("Determination of the Scattering anisotropy with optical coherence tomography", Mar. 17, 2011, 10 pages.
Rogers et al., ("Nonscalar elastic light scattering from continuous random media in the Born approximation", 2009, 3 pages.
Yi et al., ("Inverse Spectroscopic Optical Coherence Tomography: non-invasively quantifling the complete optical scattering properties from week scattering tissue", Apr. 28, 2012, 3 pages.

* cited by examiner

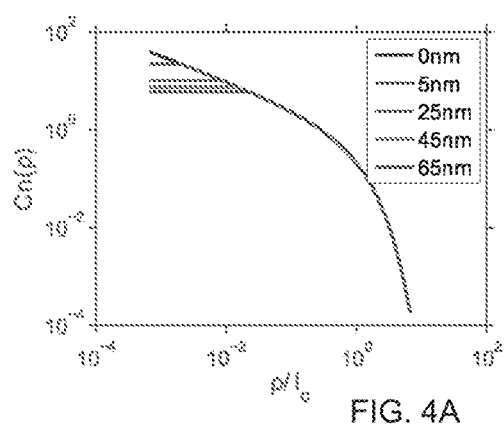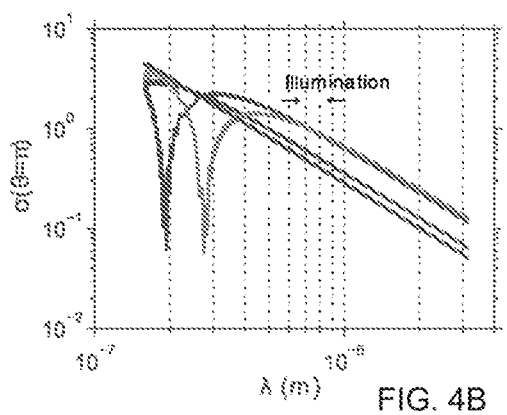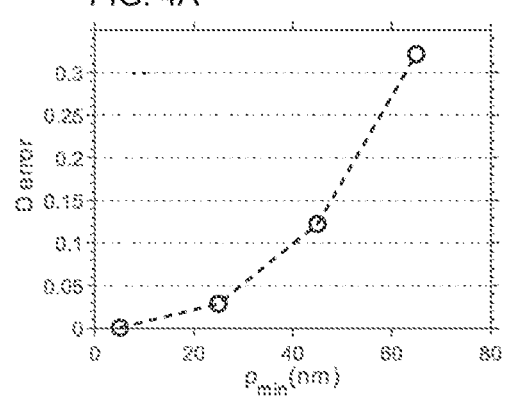
FIG. 4A
FIG. 4B
FIG. 4C

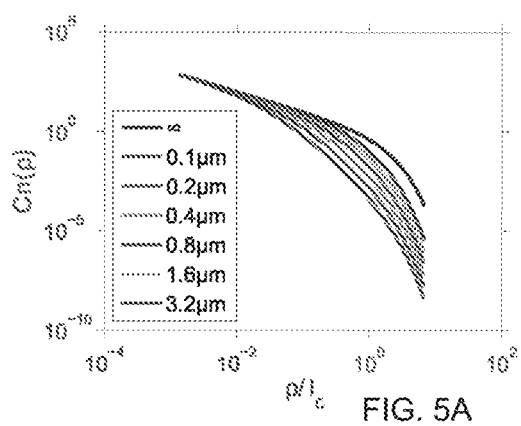
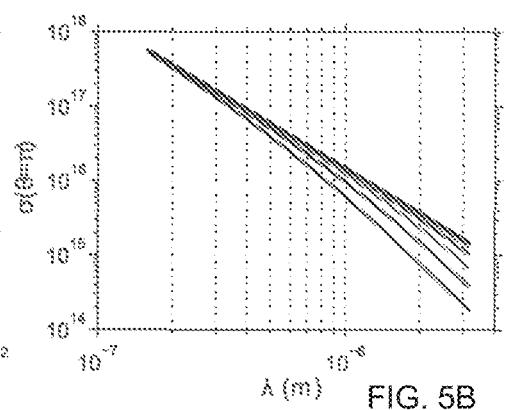
FIG. 5A
FIG. 5B
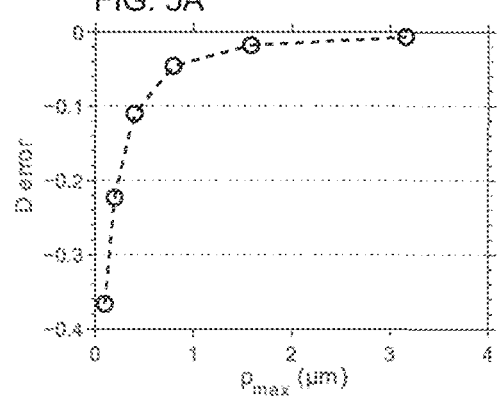
FIG. 5C $D$    0 ▬▬▬▬▬ 6

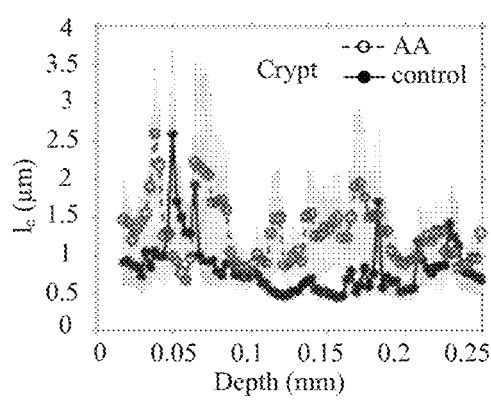
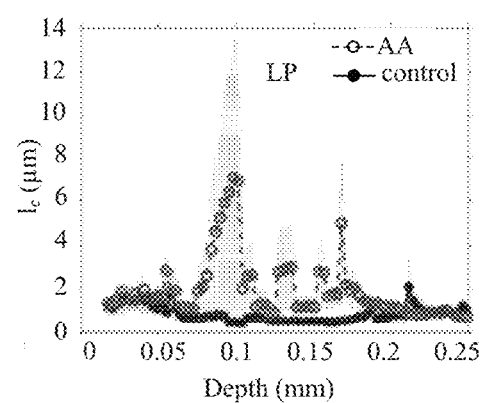
FIG. 12A
FIG. 12B

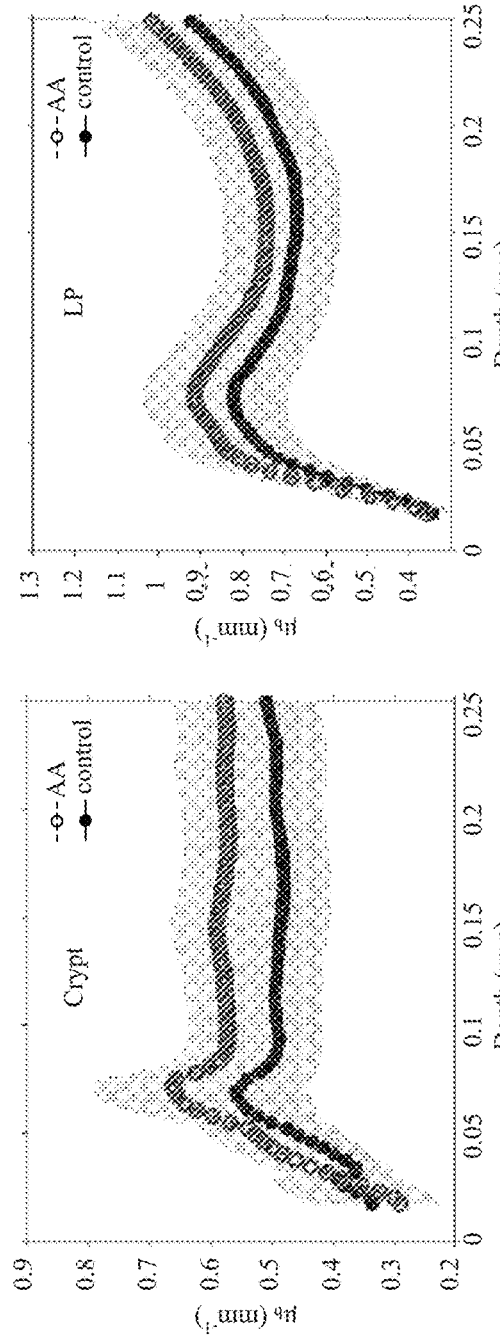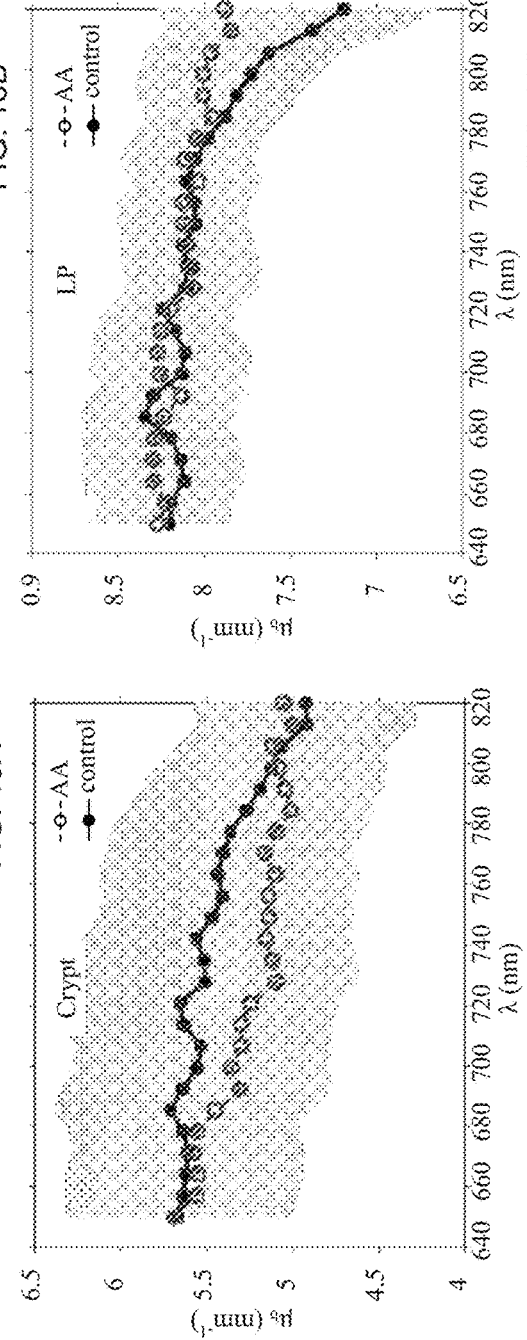
FIG. 13A, FIG. 13B, FIG. 13C, FIG. 13D

BIOLOGICAL TISSUE ANALYSIS BY INVERSE SPECTROSCOPIC OPTICAL COHERENCE TOMOGRAPHY

CROSS-REFERENCE TO RELATED APPLICATIONS

This patent arises from a continuation of U.S. patent application Ser. No. 13/651,196, filed on Oct. 12, 2012, entitled "BIOLOGICAL TISSUE ANALYSIS BY INVERSE SPECTROSCOPIC OPTICAL COHERENCE TOMOGRAPHY", which claims the benefit of U.S. Provisional Patent Application Ser. No. 61/547,365, filed Oct. 14, 2011, entitled "INVERSE SCATTERING OPTICAL COHERENCE TOMOGRAPHY (ISOCT) QUANTIFYING SUB-DIFFRACTIONAL TISSUE MASS DENSITY CORRELATION FUNCTION AND A COMPLETE SET OF TISSUE OPTICAL PROPERTIES." U.S. Non-Provisional patent application Ser. No. 13/651,196 and U.S. Provisional Patent Application Ser. No. 61/547,365 are hereby incorporated by reference herein in their entirety.

STATEMENT OF GOVERNMENT INTEREST

This invention was made with Government support under grant numbers R01CA128641 and R01EB003682 awarded by the National Institutes of Health and grant number CBET-0937987 awarded by the National Science Foundation. The Government has certain rights in the invention.

FIELD OF INVENTION

This invention relates to optical probing methods, particularly inverse spectroscopic optical coherence tomography (ISOCT), to analyze the structure of biological tissues.

BACKGROUND

Optically probing sub-diffractional biological features has always challenged researchers and clinicians. Remarkable efforts have been made to overcome this challenge from different aspects of physics. Near-field scanning optical microscopy (NSOM) collects evanescent electromagnetic waves and marked the first time that Abbe's diffraction limit was broken. Attempts to convert evanescent waves to propagating waves also led to the development of hyperlens and superlens. Stimulated emission depletion microscopy (STED), photoactivation localization microscopy (PALM) and stochastic optical reconstruction microscopy (STORM) control the switchable fluorescent reporters to resolve sub-diffractional objects in the far field, while structured-illumination microscopy (SIM) extends the collection range of the spatial frequency to achieve high resolution. Confocal light absorption and scattering spectroscopy microscopy (CLASS) utilizes Mie scattering spectrum to resolve sub-wavelength organelles without exogenous labels. More recently, spatial light interference Microscopy (SLIM) based on wave interference images nanoscale cell topography due to intrinsic scattering. Other techniques based on this interference principle such as spectral-domain optical coherence phase microscopy (SD-OCPM) are also reported. However, the challenge remains within intact tissue since the above methods are only applicable to cells.

Many of the previous attempts have required fluorescent reporters and are not able to quantify tissue structures. Furthermore, current in vivo optical measurement modalities for biological tissues are extremely challenging, because the back reflectance scheme inhibits the ability to quantify full optical scattering properties for a given sample.

Optical Coherence Tomography (OCT) is a high-resolution medical and biological imaging technology. OCT is analogous to ultrasound B-mode imaging except reflections of low-coherence light are detected rather than sound. OCT detects changes in the backscattered amplitude and phase of light. This imaging technique is attractive for medical imaging because it permits the imaging of tissue microstructure in situ, yielding micron-scale imaging resolution without the need for excision and histological processing. Because OCT performs imaging using light, it has a one- to two-order-of-magnitude higher spatial resolution than ultrasound and does not require contact with tissue.

OCT is well known to provide depth-resolved images of tissue up to approximately 1 mm. Yet the spatial resolution of these images is fundamentally limited by a temporal coherence length, which is typically greater than 1 µm and, in commercial instruments, greater than about 10 µm.

Previous attempts in the art to quantify a complete measurement of all optical light scattering properties have failed. Thus, there is a need to provide methods that enable one to acquire the spatial information of OCT at the sensitivity of sub-micron, sub-resolution length scales of light scattering.

SUMMARY

In one respect, one embodiment relates to a method for imaging a biological tissue with inverse spectroscopic optical coherence tomography (ISOCT). The method includes two steps: (a) obtaining image signal data for the biological tissue sample with spectroscopic optical coherence tomography using a calibrated instrument; and (b) quantifying the image signal data. The quantifying of the image signal data is accomplished by either quantifying a tissue mass density correlation function with a length scale of sensitivity in sub-diffractional regime from the optical coherence tomography spectra for each three-dimensional voxel of spatial resolution, or quantifying a full set of optical scattering properties of the image signal data in a spatially-resolved, three-dimensional space.

In a second respect, one embodiment relates to a method for enhancing image contrast for a biological tissue. The method includes three steps: (a) obtaining image signal data for the biological tissue sample with spectroscopic optical coherence tomography with a calibrated instrument (b) obtaining a plurality of D values; and (c) generating a Hue-Saturation-Value color space plot based upon the image signal data as a function of the plurality of D values.

In a third respect, one embodiment relates to a system for use in inverse spectroscopic optical coherence tomography (ISOCT). The system includes a processor operatively coupled to a memory. One or both of the processor and the memory are operable to perform two steps: (a) quantify a tissue mass density correlation function with a length scale of sensitivity in sub-diffractional regime, and (b) quantify a full set of optical scattering properties of microscopic tissue in a spatially-resolved, three-dimensional space.

BRIEF DESCRIPTION OF THE DRAWINGS

FIG. 4 depicts the numerical simulation of sensitivity analysis of D at minimum length scale perturbation on the RI correlation function.

FIG. 5 depicts the numerical simulation of sensitivity analysis of D at maximum length scale perturbation on the RI correlation function.

FIG. 12 illustrates an $l_c$ analysis between advanced adenoma (AA) and control colon samples as in detection of colon cancer field effect for crypt (FIG. 12a) and laminar propria (LP) (FIG. 12b).

FIG. 13 illustrates a $\mu_b$ (FIGS. 13a and 13b) and $\mu_s$ (FIGS. 13c and 13d) analysis between advanced adenoma (AA) and control colon samples as in detection of colon cancer field effect for crypt (FIGS. 13a and 13c) and laminar propria (LP) (FIGS. 13b and 13d).

DETAILED DESCRIPTION OF THE INVENTION

Figure 1A:
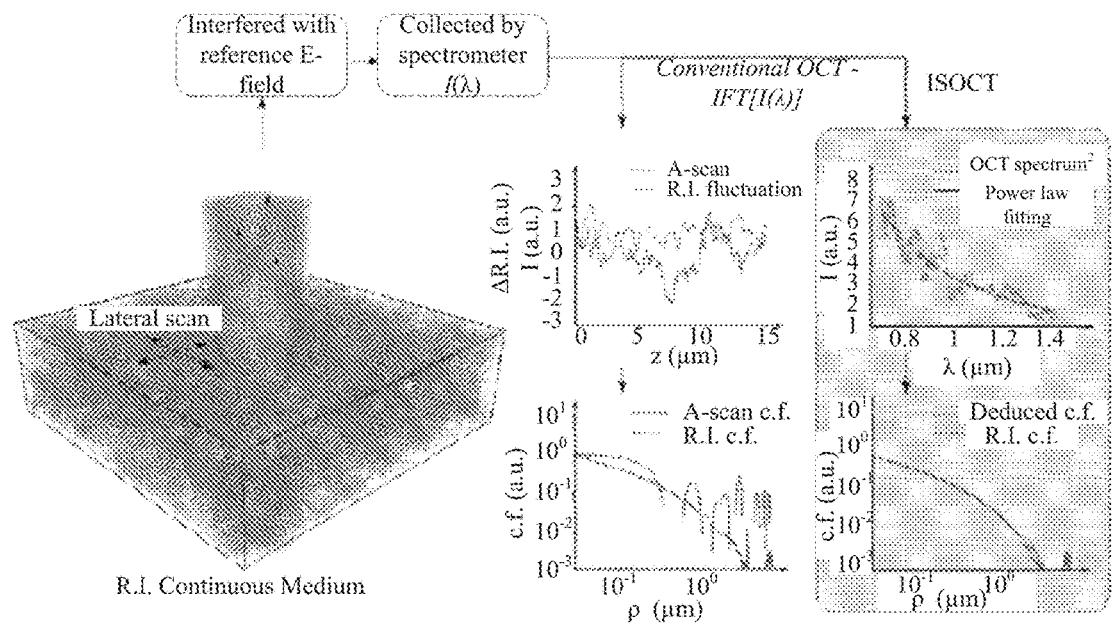
FIG. 1 depicts a scheme of the ISOCT principle (FIG. 1a) and confocal illumination geometry in an exemplary ISOCT sample arm (FIG. 1b).

Applicants have developed a novel, robust method termed inverse spectroscopic OCT (ISOCT) that enables one to quantify mass density correction functions and to measure a complete set of the optical properties for a tissue structure without any prior knowledge of the underlying structure of that tissue. The method enables detailed analysis of biological tissues at spatial resolutions previously unattainable. In this respect, the systems and method disclosed herein provide powerful imaging tools for use in a variety of biological investigations, including incisive pathological determinations and clinical diagnoses. In particular, the disclosed method and system enable detection of alterations in density correlation functions that can be used as accurate biomarkers of carcinogenesis and other disease states.

The method and system disclosed herein combine the sensitivity of sub-micron sub-resolution length scales of light scattering with the three-dimensional imaging capability of OCT. Thus, the imaging method can assess tissue structure at length scales considerably less than 1 µm. Such measurements are accomplished through an analysis of a spectral profile of an OCT signal and a measurement of a functional form of a fundamental property of tissue structure. By combining the scattering and backscattering coefficients, as measured with the disclosed ISOCT method, the full mass density correlation function and the complete set of optical scattering properties can be quantified from a microscopic tissue region in 3D.

ISOCT can quantify tissue mass density correlation function with length scale of sensitivity in sub-diffractional regime to approximately 40 nm. Light scattered elastically from biological tissue is originated from the heterogeneity of the microscopic structure, or in other words, tissue mass density distribution. In tissue, the mass is mostly composed of macromolecules such as, for example, proteins, lipids, deoxyribonucleic acid (DNA), etc. and the mass density is linearly proportional to refractive index (RI) of the scattering medium. The tissue structure can be quantified using the RI fluctuation correlation functions that are parameterized by a Whittle-Mate'rn functional family. Under a modified Born approximation, the wavelength dependent OCT signal is measured to quantify the RI correlation function form. The ratio of backscattering and scattering coefficient is measured to quantify a deterministic length scale and RI fluctuation variation in the correlation function. Accordingly, the exact form of mass density correlation function can be quantified.

ISOCT can quantify a full set of optical scattering properties of microscopic tissue that is spatially resolved in three-dimensional space. Quantifying full scattering properties in vivo can be extremely difficult in any optical modalities due to the back reflectance detection scheme for noninvasive measurements. Since the tissue mass density correlation function can be quantified with ISOCT, full optical properties including reduced scattering coefficient, anisotropic factor and the scattering phase function can be derived directly. The interferometry detection scheme provides means to isolate signal from spatially resolved microscopic region in three-dimensional spaces.

ISOCT Methodology and Principles

FIG. 1 illustrates the ISOCT principle (FIG. 1a). FIG. 1a (left) shows a turbid RI medium numerically generated according to a power-law RI correlation function. Conventional FDOCT performs an inverse Fourier transform (IFT) on the entire bandwidth of the interference spectrum to the A-scan depth profile. The OCT A-scan signal from the actual RI fluctuations at each lateral position (FIG. 1a, top middle) can be simulated, from which the A-scan correlation function can be calculated. By way of comparison, ISOCT averages OCT spectra extracted from the same locations and fitted with a power-law to recover the RI correlation functional type. Though conventional OCT already provides a 3D morphological map of tissue, the limited resolution and speckle effects prevent an accurate estimation of the true RI correlation function. By applying imaging and quantitation using ISOCT, the RI correlation functional form can be indirectly deduced that yields a more accurate result (Fig. 1a, bottom right).

Figure 1B:
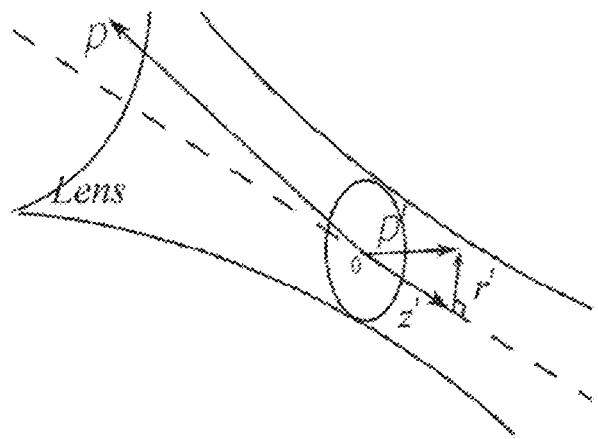

Referring to FIG. 1b, the confocal scheme is adapted for coherent illumination in which a scanning Gaussian beam is projected onto tissue by an objective lens. After acquisition of the interference signal by a spectrometer, a short frequency Fourier transform (SFFT) is performed to obtain ISOCT spectrum from a probed volume usually on the order of ten microns in both axial and lateral extent. In a weakly scattering medium like biological tissue, a modified first-order Born approximation is applied under the condition that the depth of focus is much larger than the probed volume, so that the illumination can be approximated as a Gaussian pencil beam.

The square intensity of SOCT is proportional to the backward scattering power spectrum, as presented in Eqn. 1:

$$I^2 = rI_0^2 \frac{\mu_b}{4\pi} L\exp(-2zn\mu_s). \quad \text{(Eqn. 1)}$$

where $I_0$ and $L$ is the intensity and the temporal coherence length of the incidence, respectively; $r$ is the reference reflectance coefficient; $z$ is the depth and $n$ is the mean RI of the tissue, taken as 1.38; $\mu_b$ and $\mu_s$ are the backscattering coefficient and the scattering coefficient, respectively.

A Whittle-Mate'rn functional family is applied to describe the RI fluctuation correlation function so that $\mu_b$ and $\mu_s$ can be derived and incorporated into Eqns. 2 and 3, respectively:

$$\mu_b = N_c 8\sqrt{\pi}\,\Gamma(D/2)k^4 l_c^3 (1 + [2kl_c]^2)^{-D/2}. \quad \text{(Eqn. 2)}$$

$$\mu_s = \quad \text{(Eqn. 3)}$$
$$N_c \frac{\sqrt{\pi}\,\Gamma(D/2-3)}{2k^2 l_c^3}[(1 + (2k^2 l_c^2(D/2-2)-1)\times 2k^2 l_c^2(D/2-3)) - (1 + 2k^2 l_c^2(D/2+1) + 4k^4 l_c^4(4-3D/2+D^2/4))(1+4k^2 l_c^2)^{1-D/2}].$$

where $l_c$ determines the upper length scale of the correlation function, beyond which the function rolls off to 0 quickly, $N_c$ is a scaling factor representing the variance of the RI fluctuation, $N_c$ is related to the RI variance $dn^2$ by Eqn. 4:

$$N_c = \frac{dn^2}{\left|\Gamma\left(\frac{D}{2} - \frac{3}{2}\right)\right|}. \quad \text{(Eqn. 4)}$$

The term D is a deterministic factor defining the correlation function form. When 0<D<3, the correlation function has the form of the power law suggesting the tissue is organized in a fractal manner where D defines the mass fractal dimension ranging from 0 to 3 in Euclidean space. When D=4, the correlation function evolves into exponential and approaches Gaussian function when D approaches infinity. In qualitative terms, a smaller D value indicates more drastic change of RI in smaller length scale, or a smaller length scale of tissue heterogeneity.

Tissue usually satisfies $kl_c \gg 1$ and $D>2$. Under this condition, the expression of $\mu_b$ and $\mu_s$ can be simplified to yield Eqn. 5:

$$\mu_b = 2^{3-D} N_c \sqrt{\pi}\,\Gamma(D/2) l_c^{3-D} k^{4-D},\ (kl_c \gg 1)\ \mu_s = 2N_c \sqrt{\pi}\,\Gamma(D/2-1)k^2 l_c,\ (kl_c \gg 1\ \&\ D>2); \quad \text{(Eqn. 5)}$$

thus, the reflection albedo $\alpha$, defined as here as the ratio of $\mu_b$ and $\mu_s$, can then be written as a simplified form in Eqn. 6:

$$\alpha \approx \Gamma(D/2)/\Gamma(D/2-1)(2kl_c)^{2-D}. \quad \text{(Eqn. 6)}$$

Figure 2:
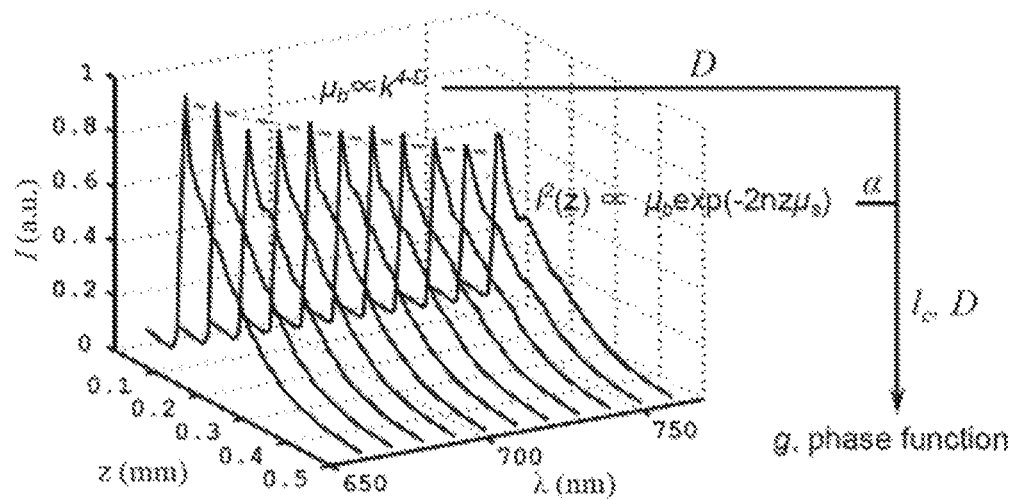
FIG. 2 illustrates a schematic of the ISOCT methodology. D is obtained from power law fitting to $\mu_b$ spectrum, $l_c$ is deduced by D and α according to Eqn. (6).

As FIG. 2 shows, the maximum value of the $I^2$ measures $\mu_b$; and the decay rate along depth measures $\mu_s$ based on Beer's law. Thus, the reflection albedo $\alpha$ can be calculated.

Further, the spectrum dependency of $\mu_b$ can be analyzed by the time-Fourier analysis in spectroscopic OCT and fitted with a power-law equation. The exponent (often called the scattering power, SP) is equal to 4-D according to Eqn. 5. With D and $\alpha$, $l_c$ can be deduced. Then the correlation functional form can be readily described by D and $l_c$. Therefore, the phase function and the anisotropic factor g can be quantified. $N_c$ can be then calculated after incorporating $\mu_b$, $l_c$ and D value in Eqn. 5. And the RI variance can be quantified by Eqn. 4.

Several steps of data processing can be performed initially including, for example, normalization by the spectrum from the reference arm, a DC component subtraction and a re-sampling into evenly spaced k domain spectrum. The SFFT method can then be applied to extract the spatial-resolved OCT spectra with the wavelet window to be a FWHM=15 nm Gaussian window. A detailed procedure of data processing is described in Example 1.

The ISOCT system is calibrated before imaging studies so that one will be able to normalize a recorded signal. Calibration procedures include a test for self-reflections (for example, recording reflected signal when no sample is placed) and a test for spectral response (for example, a "white" reflection standard). Such calibration tests are well known in the art.

To eliminate the systematic error on the spectral response, a solution containing 80 nm polystyrene beads (~1.7%-2.0% (wt/wt)) can be imaged and processed at various depths in the same manner whose OCT spectra are used for a second normalization. The 80 nm beads are preferable for this application because they behave as dipole scattering agents, and the wavelength-dependent spectrum is provided by Mie theory. The normalization spectra of the beads in terms of depth can be interpolated into a 2D map to exclude a slight systematic chromatic aberration.

The ISOCT method and system can be validated with any media having defined ultrastructural features. Examples of such media include certain tissue engineered models, such as collagen matrix, and particles of known size suspended in a liquid phase medium (for example, aqueous solution) or a solid phase medium (for example, agarose). Particles are generally preferred, as tissue engineered models and other irregularly shaped objects would require high resolution imaging such as electron microscopy to define the relevant ultrastructural features.

Validations are preferably accomplished using a phantom design having a plurality of objects of discrete sizes and uniform shapes, wherein the sizes, shapes and concentration ratios of the objects are known. Preferred phantom objects include nanospheres of defined size, wherein each has a distinct wavelength dependent backscattering cross section calculated from Mie theory. Preferred material compositions of such nanospheres include polystyrene, silica and $TiO_2$, among others. Polystyrene is a highly preferred composition of such nanospheres for the phantom design.

The ISOCT method measures three quantities: D value, backscattering and scattering coefficients $\mu_b$ and $\mu_s$. Calibration for these quantities is provided to evaluate the precision of the measurements. For calibrating D value measurement, phantoms were designed using sub-wavelength polystyrene nanospheres. A careful choice of sizes and composition can mimic a power law spectrum from a continuous medium defined by the Whittle-Mate'rn correlation function. Typically a set of four types of polystyrene nanospheres having a range of diameters (for example, 360 nm, 300 nm, 200 nm and 80 nm) in a defined concentration ratio (for example, 2:5:20:50 (parts per given diameter particle ranging from largest particle size to smallest particle size)) is prepared.

FIG. 3 illustrates a calibration of a D value measurement. FIG. 3a shows an example of using four sizes of nanospheres phantom, wherein each of the nanospheres has distinct wavelength dependent backscattering cross section calculated from the Mie theory. Individual $\mu_b$ from each nanospheres is also shown. The total $\mu_b$ is the summation of all the particles. The ensembled $\mu_b$ eliminates the oscillation from individual type of nanospheres and produces a power law spectrum behavior over the illumination range. Independent measurements from each phantom were carried out and each D value was calculated from OCT spectra averaged over a 0.04 mm$^2$ area. FIG. 3c illustrates a calibration of the D value with a set of exemplary phantoms. The error bar represents a standard deviation across independent measurements. Example 1 and FIGS. 3-5 provide detailed procedures that illustrate further aspects of D value calibration, a statistical robust analysis of D measurement, and simulations of sensitivity analysis of D as a function of length scale perturbation on the RI correlation function.

Figure 6A:
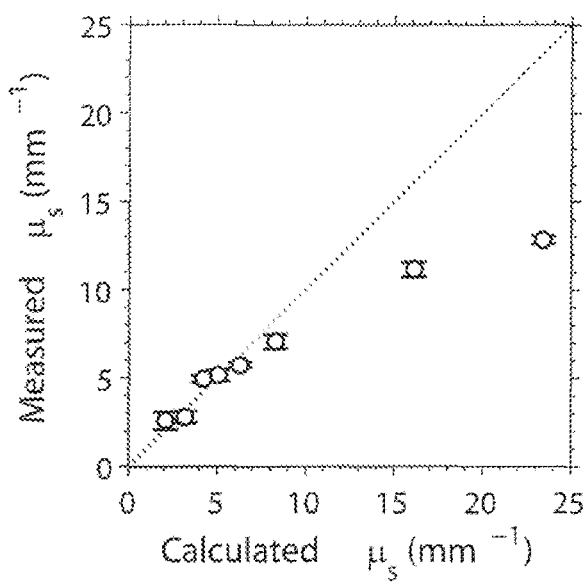
FIG. 6 depicts a calibration of $\mu_s$ (FIG. 6a) and $\mu_b$ (FIG. 6b).
Figure 6B:
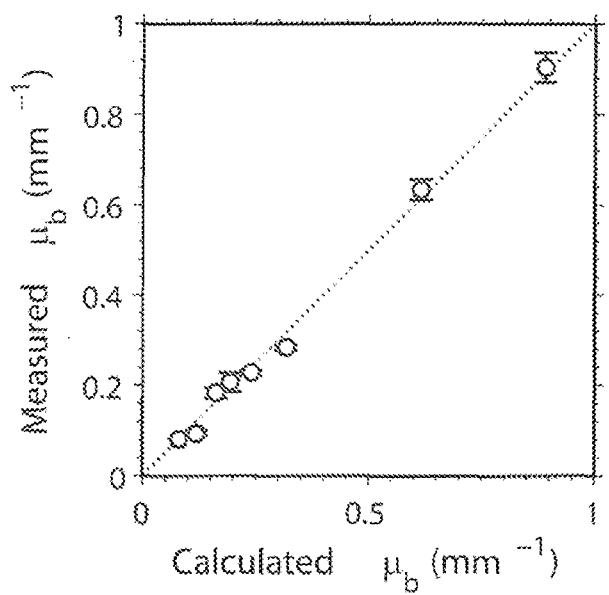

To calibrate the measurement of $\mu_b$ and $\mu_s$, 0.82 μm beads phantom was made with 1% agarose gel and imaged with ISOCT. The $\mu_b$ and $\mu_s$ from the phantom were linearly proportional to the concentration of the beads under the Born approximation and calculated with the Mie theory. The absolute intensity magnitude and the intensity decay rate along penetration depth were linearly associated to $\mu_b$ and $\mu_s$ and linear scaling constant factors are chosen to quantify $\mu_b$ and $\mu_s$. The calibrations of $\mu_s$ and $\mu_b$ are depicted in FIGS. 6a and 6b, respectively. The calibration curves shown in FIG. 6 are in good agreement with that found for the calculated value in the typical physiological ranges. Some units may be in mm$^{-1}$ and a measured value may be averaged at 720 nm. When $\mu_s$ was over 10 mm$^{-1}$, the measured value was underestimated due to the multiple scattering effects in strong scattering medium. However, most biological tissues have scattering coefficients lower than 10 mm$^{-1}$ and fall with the linear region of $\mu_s$ calibration.

ISOCT Imaging Systems and Instrumentation

Figure 7A:
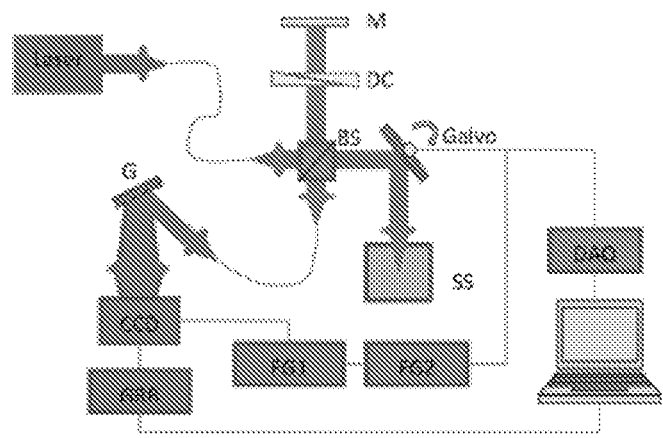
FIG. 7 depicts a "bench-top" ISOCT instrumentation system (FIG. 7a) and a fiber optic probe-based ISOCT system (FIG. 7b).
Figure 7B:
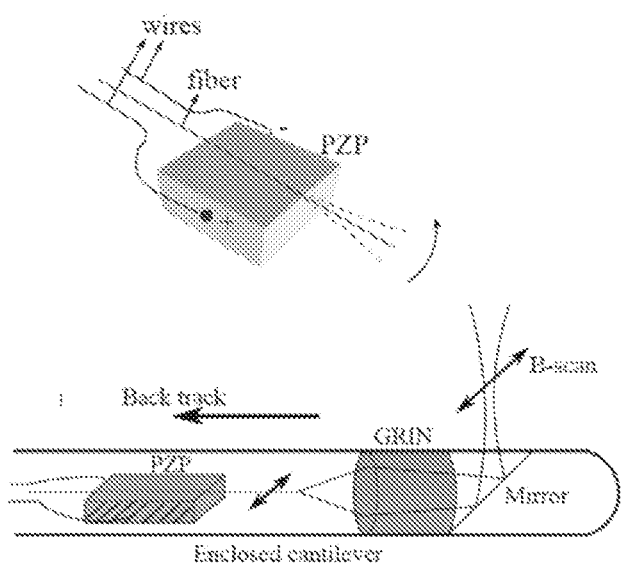

Referring to FIG. 7, ISOCT imaging systems can be configured as a "bench-top" instrumentation system for the analysis of biological tissues ex vivo (for example, analysis of pathological samples or biopsies) and accessible external tissues in vivo (for example, skin surfaces of patients) (FIG. 7a). Handheld instruments also fall within the scope of the disclosure, wherein the ISOCT method may be used in the field or in mobile or portable applications. The ISOCT imaging systems can also be adapted to include a fiber optic based probe for analysis of internal biological tissues in vivo (for example, internal organ tissue of patients) (FIG. 7b).

Referring to FIG. 7a, such a system generally comprises a laser source coupled to a single mode fiber, an interferometer, a sample stage, a CCD camera and a computer. The interferometer provides additional elements related to processing the incident radiation from the laser to split the beam into sample and reference arms and to processing the reflected radiation from the sample and reference arms for spectral image analysis. The CCD camera is used to collect the processed image signals from the interferometer. The computer controls the interferometer and camera functions for data acquisition. Preferably, high speed hardware such as a digital signal processor and a field-programmable gate array can be used to implement the image processing. A detailed description of an exemplary bench-top instrumentation system is presented in Example 1.

Referring to FIG. 7b, ISOCT method is also amenable to a fiber optic based implementation. The following design can provide for a fiber optic ISOCT probe less than 1 mm in diameter. While conventional OCT probes require a circular scan of the beam driven by an external rotor or an internal spiral track, those mechanical parts limit probe miniaturization. To keep the probe size less than 1 mm, a scanning mechanism based on a piezo plate (PZP) actuator can be used. A single mode fiber branched from a fiber coupler (interferometer for OCT) is glued onto the plate. When a sinusoidal waveform is applied on the PZP, the fiber tip oscillates along the vibration direction and form a stable resonance scan (the B-scan in FIG. 7b). A gradient-index (GRIN) lens follows PZP and the fiber tip. The GRIN lens is used to focus the light and also to collect the backscattered light. A reflective mirror is attached to the end of the GRIN lens to steer the light onto the tissue. All the miniature optics can be enclosed in a cantilever, which is retracted at a set speed to realize the scan in the other lateral direction. Thus, a 3D image can be generated after the retrieval of the cantilever and the ISOCT analysis performed.

The ISOCT method and system can be realized in hardware, software, or a combination of hardware and software. These elements can be organized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The ISOCT method can be embedded in a computer program product, which comprises all the features enabling the implementation of the methods described herein, and which is able to carry out these methods when loaded in a computer system. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The ISOCT method and system contemplate one or more processors operatively coupled to one or more memories (for example, a non-transitory computer readable medium) in which one or more steps described herein are stored as instructions or executable code in the one or more memories and are executed by the one or more processors or are used to configure the one or more processors. The one or more processors and the one or more memories can be part of a computer system, such as part of an integrated circuit, an application specific integrated circuit (ASIC), a single integrated circuit chip, or combinations thereof. The computer system maybe part of, for example, laboratory equipment or medical equipment.

The ISOCT method and system contemplate using software, hardware and/or firmware, including combinations thereof. A software algorithm can be installed in commercially available OCT devices to identify tissue elements at the nanoscale, for example, between approximately 40 nm to approximately 1000 nm. The software algorithm may compute, for example, mass density correlation functions with a voxel—thus for mass scales between approximately 40 nm and approximately 1000 nm—from a spectral profile of an OCT signal. The software algorithm solves an inverse scattering problem that arises when trying to determine the characteristics of tissue (e.g., the distribution of refractive indices across the tissue sample) from measurement data of radiation from the tissue (e.g., scattering). The software algorithm can be realized, for example, in Matlab, C, C++, Pascal, Java, Fortran, Perl, Basic, machine language or other programming languages. Preferably, the software can be written in C++ and uses a WINDOWS® operating system (Microsoft Corporation).

To any extent to which specific processing hardware is provided to realize the algorithm, some embodiments according to some aspects of the present invention provide for digital signal processors and/or field programmable gate array, etc. A data interface with an existing OCT system can be implemented to provide raw data, which includes spectral data directly output from a detector (for example, a line scan camera or photo diode).

The ISOCT method and system contemplates the use of one or more of the following: lenses; electrical, magnetic, electromagnetic and/or optical sensors; electrical, magnetic, electromagnetic and/or optical receptors; signal processors; digital processors; digital signal processors; filters; amplifiers; correlators; interferometers; spectrometers; projectors; light sources; electromagnetic wave sources; imagers; scanners; endoscopes; microscopes; video equipment; and displays.

Thus, one preferred embodiment includes a system for use in inverse spectroscopic optical coherence tomography (ISOCT). The system includes a processor operatively coupled to a memory needed for executing at least one algorithm of ISOCT. Preferably, the one or both of the processor and the memory are operable to execute the instructions to quantify a tissue mass density correlation function with a length scale of sensitivity in sub-diffractional regime from the optical coherence tomography spectra for each three-dimensional voxel of spatial resolution. Preferably, either in the alterative or in addition, the one or both of the processor and the memory are operable to execute the instructions to quantify a full set of optical scattering properties of microscopic tissue in a spatially-resolved, three-dimensional space.

A series of steps are performed to process data from the ISOCT instrumentation (FIG. 7). These steps include: (1) 3D and 4D OCT image data generation; (2) data normalization; (3) data averaging; (4) D value, $\mu_b$ and $\mu_s$ calculation; (5) attenuation correction; and (6) term $dn^2$ deduction. Example 1 provides a more detailed description of these steps.

The instrumentation and systems suitable for the ISOCT method are calibrated for obtaining the D value, backscattering coefficient $\mu_b$ and scattering coefficient $\mu_s$. Once the D value, backscattering coefficient $\mu_b$ and scattering coefficient $\mu_s$ are calibrated for a given instrument, the method may be used with the instrument to measure and image the full set of optical scattering properties for a biological tissue using ISOCT. As used herein, "calibrated instrument" refers to an instrument that is calibrated for obtaining the D value, backscattering coefficient $\mu_b$ and scattering coefficient $\mu_s$.

Application of ISOCT Imaging to Biological Tissues

ISOCT provides full optical scattering properties that can be depicted from a spatially resolved microscopic tissue region. The ISOCT method can be used to obtain information about the tissue sub-diffractional structural changes, thereby enabling detailed analyses of biofunctionality in situ, wherein both cells and extracellular matrix behave in their most natural way. For example, chromatin decondensation in epithelial cells has been implicated in dysplasia and hyperplasia, which can lead to carcinogenesis. The nuclei mass distribution will be changed while chromatin is unraveled to be hyper-productive. Evidence also indicates that extracellular structure change from stroma can be a substantial marker for various types of epithelial cancers. And studies involving subtle mass transport or transformation in cellular level or extracellular matrix can utilize this approach to achieve high sensitivity physical structural mutation without any exogenous contrast agents. Thus, systems and methods of ISOCT can be a powerful imaging tool in biological investigations and for clinical diagnosis since alterations in density correlation function can be used as accurate biomarkers of carcinogenesis and other disease states.

Figure 9A:
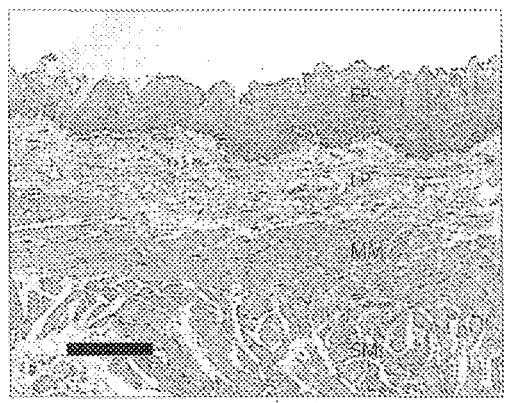
FIG. 9 illustrates the following for an ex vivo rat esophageal tissue: a tissue histology (FIG. 9a); an original OCT intensity map lot (FIG. 9b); a pseudo-color map plotted in a HSV color space to show image contrast enhancement (FIG. 9c); and intensity and D depth profiles (FIG. 9d).

Example 2 provides an application of the ISOCT method in the imaging of an ex vivo, rat esophageal tissue sample in which epithelium (EP), laminar propria (LP), muscularis mucosa (MM) and submucosa (SM) are illustrated. A stratified structure of EP, LP, MM and SM can be identified in OCT images in FIG. 9b with comparison to the histology in FIG. 9a.

Additional rat organs were measured ex vivo to demonstrate the feasibility of ISOCT. The scattering coefficient $\mu_s$ and backscattering coefficient $\mu_b$ were calculated from the entire illumination bandwidth (630 nm to 800 nm), so that $l_c$ is calculated at the center wavelength 710 nm in Eqn. (6). With D and $l_c$, g was obtained for the different types of organs. The key parameters of the tested organs from one subject are summarized in Table 1.

To justify these measurements, the g values of similar organs from the literature are listed as comparison. Each measurement is taken over 0.25×0.25 mm² area in x×y and from the top 100 µm tissue.

TABLE 1

| Physical and Optical Properties ± s.e. of Different Rat Organs (710 nm) | | | | | | |
|---|---|---|---|---|---|---|
| Organ | N | D | $\mu_s$ (mm$^{-1}$) | $\mu_b$ (mm$^{-1}$) | $l_c^{(1)}$ | $g^{(1)}$ | $g^{(2)}$ |
| Brain | 6 | 2.80 ± 0.21 | 10.81 ± 0.28 | 0.65 ± 0.08 | 0.76 ± 0.29 | 0.87 ± 0.05 | 0.88 (630 nm) |
| Liver | 10 | 2.36 ± 0.11 | 10.32 ± 0.29 | 0.49 ± 0.03 | 4.05 ± 1.52 | 0.91 ± 0.02 | 0.95 (630 nm) |
| Lung (deflated) | 9 | 3.02 ± 0.20 | 11.42 ± 0.29 | 0.11 ± 0.02 | 1.75 ± 1.04 | 0.95 ± 0.04 | 0.95 (630 nm) |
| Heart | 9 | 2.84 ± 0.08 | 13.26 ± 0.37 | 0.27 ± 0.06 | 2.59 ± 0.96 | 0.96 ± 0.02 | 0.973-0.983 (1060 nm) |
| Intestine | 7 | 3.06 ± 0.15 | 7.80 ± 0.23 | 0.05 ± 0.01 | 2.78 ± 1.42 | 0.97 ± 0.03 | |
| Spleen | 7 | 2.98 ± 0.19 | 13.28 ± 0.30 | 0.26 ± 0.09 | 1.71 ± 1.13 | 0.95 ± 0.03 | |

[1]Data were deduced and averaged from each measurement.
[2]g data from the literature.

Figure 10A:
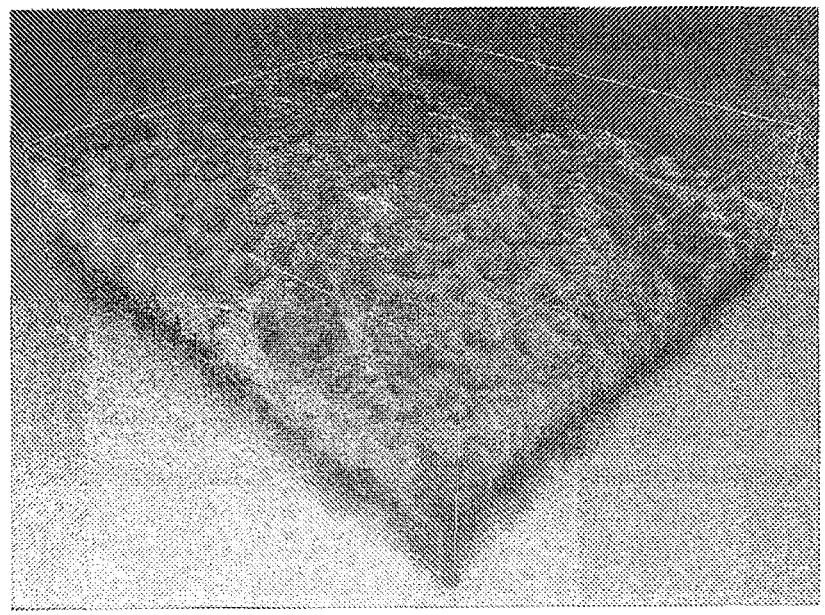
FIG. 10 illustrates the following for a human colon tissue biopsy: 3D images of tissue (FIGS. 10a and 10b); tissue mass density correlation function parameters (FIGS. 10c, 10d and 10e); and optical properties in terms of uniform penetration depth (FIGS. 10f, 10g and 10h).
Figure 10B:
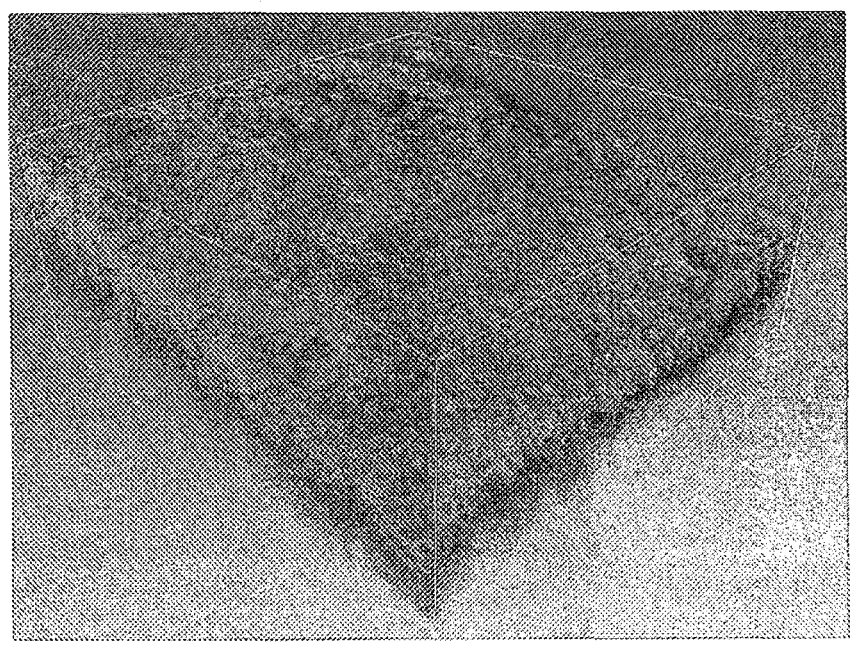
Figure 10C:
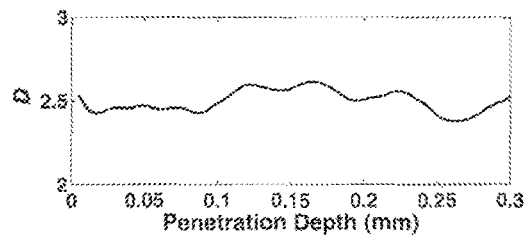
Figure 10D:
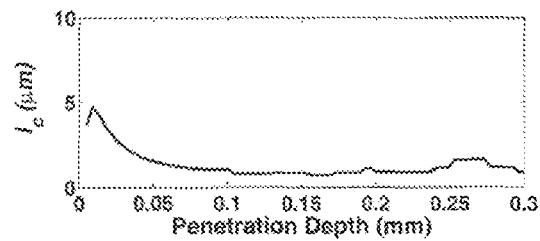
Figure 10E:
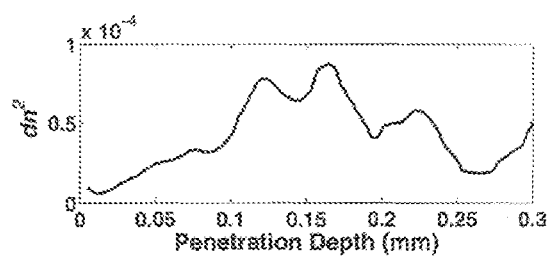
Figure 10F:
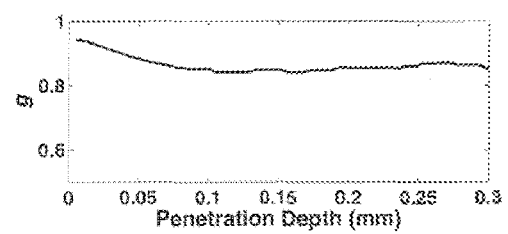
Figure 10G:
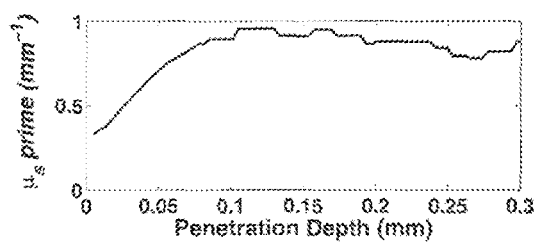
Figure 10H:
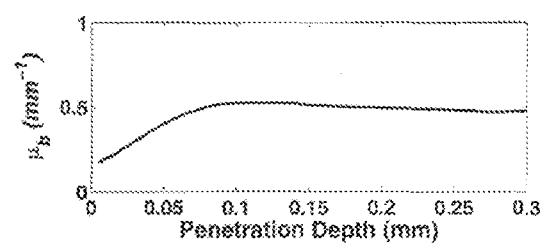

Example 3 provides an application of the ISOCT method in the imaging of a human colon tissue biopsy. The method can enable extraction of anisotropic factor g and D value (FIGS. 10a and 10b); tissue mass density correlation function parameters (FIGS. 10c, 10d and 10e); and the full set of optical parameters (FIGS. 10f, 10g and 10h).

Figures 11A, 11B:
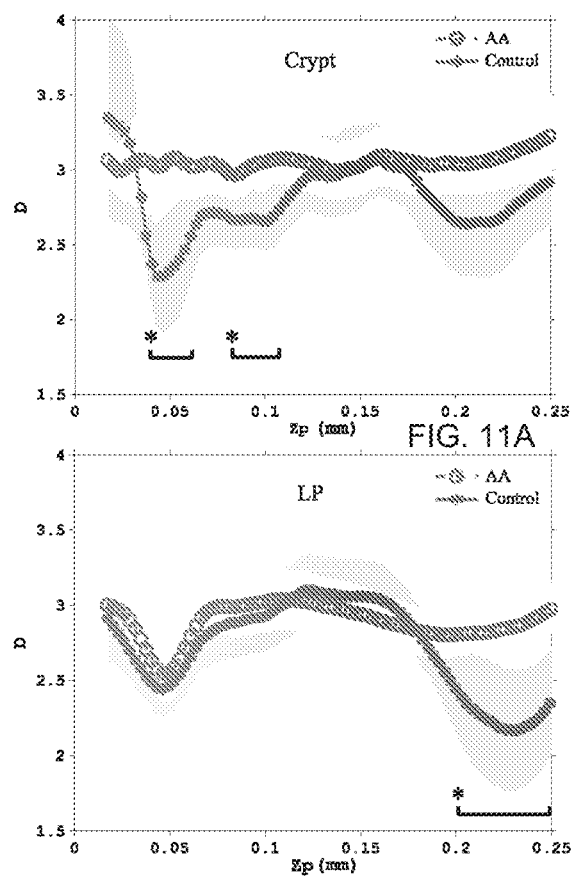
FIG. 11 illustrates detection of colon cancer field effect by measuring D for Crypt (FIG. 11a) and laminar propria (LP) (FIG. 11b). The D±SE curve along the penetration depth on the crypts and on the LP (AA: n=13, control: n=10). The light color area depicts the standard error. *P<0.1 is calculated by one tail two sample t-test.

Example 4 describes an application of the ISOCT method for the detection of early stage cancer (FIGS. 11-13). ISOCT spectra were recorded from rectal biopsies (n=74 subjects, 21 with advanced adenomas) having the following features: (a) a mass density correlation function $C_n(\pi)$ had a mass fractal form, and its fractal dimension D was increased in early stage cancers; (b) the reduced scattering coefficient $\mu'_s$ was decreased, and (c) the anisotropy coefficient g was increased in colonocytes.

Thus, the ISOCT imaging method can provide numerous advantages for clinical diagnostics. For examples, the method can detect alterations in tissue that are otherwise below the resolution of conventional histopathology and microscopy, and the method renders 3D imaging of tissue, which provides more leverage for tissue analysis and translates into better, more robust diagnostics.

From the tissue measurements, biological tissue is organized in mass fractal regime and therefore, and D value can directly quantify the mass fractal dimension. Furthermore, the physical and the optical properties can be extracted from microscopic region in three-dimensional space providing an excellent tool to perform microscopic structure analysis. The length scale of sensitivity to approximately 40 nm for quantifying fractal dimension; thus, sub-diffractional quantification can be done in intact tissue.

Thus, a method for imaging a biological tissue with inverse spectroscopic optical coherence tomography (ISOCT) is preferably accomplished in the following manner. One initially obtains image signal data for the biological tissue sample with spectroscopic optical coherence tomography using a calibrated instrument. One can obtain image signal data by actually performing an analysis of a biological tissue on site, for example with a bench-top, hand-held or fiber optic ISOCT instrumentation. Alternatively, one can be obtain image signal data by being provided such data from another who performed an analysis of a biological tissue at a remote site, for example with a bench-top, hand-held or fiber optic ISOCT instrumentation. Once such image signal data is obtained, one then quantifies the image signal data using one or more algorithms, or a combination of such algorithms, as described herein. Preferably, one can quantify a tissue mass density correlation function with a length scale of sensitivity in sub-diffractional regime from the optical coherence tomography spectra for each three-dimensional voxel or spatial resolution. Preferably, either in the alternative or in addition, one can quantify a full set of optical scattering properties of the image signal data in a spatially-resolved, three-dimensional space.

The ISCOT imagine method and instrumentation systems can be implemented for any biological tissue. As used herein, "source of biological tissue" refers to organs, tissues, samples, extracts, biopsies, explants, implants, transplants, grafts, engineered biologically compatible materials, and the like, which reside within a biological organism, which can be adapted for physiological or biophysical purpose within a biological organism, or which can be obtained from a biological organism, whether living or dead. As used herein, "type of biological tissue" refers to biological tissues from particular organs and tissue systems having physiological functions and, with respect to mammals, include adrenal gland, anus, auditory organs (for example, ear), bladder, brain, breast, blood vessels, cardiac tissue, cardiovascular system tissues, colon, connective tissue, epithelial tissue, esophagus, eye, gall bladder, heart, intestine, kidneys, larynx, limbs, liver, lung, lymphatic system tissues (for examples, thymus, lymph, nodes, etc.), mouth, muscle, neck, nervous system tissue (for example, spinal cord), nose, olfactory, pancreas, parathyroid gland, pineal gland, pituitary gland, prostate, sexual organ tissues (for examples, cervix, vagina, penis, etc.), sinus, skin, spleen, stomach, throat, tongue, thyroid gland, rectum, renal system tissues, reproductive tissues (for examples, ovaries, uterus and testicles), among others.

Preferably, "biological organism" refers to a plant or animal composed of at least one tissue and/or organ system in a differentiated and/or undifferentiated form (for example, containing stem cells and/or terminally differentiated cells, respectively) and in a normal and/or non-normal form (for example, healthy vs. microbially-infected, diseased, or cancerous states). More preferably, biological organism refers to an animal (for examples, amphibians, birds, fish, mammals, reptiles, and invertebrates) having a differentiated, multiple organ physiology and metabolism system. Most preferably, biological organism refers to a mammalian animal, such as a human, dog, cat, hamster, mouse, monkey, rat, pig, cow, horse, among others. Human is a highly preferred mammal for use with the ISOCT imaging method and system.

Image Contrast Enhancement

Figures 14A, 14B, 14C, 14D:
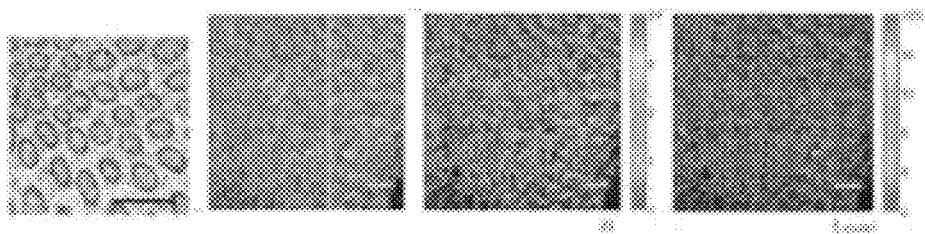
FIG. 14 illustrates an ex vivo human colon biopsy to demonstrate the image contrast enhancement power of the ISOCT method as described herein. The arrows designated as "C" denote examples of crypts; the bar denotes a 200 µm length standard.
Figures 14E, 14F, 14G, 14H:
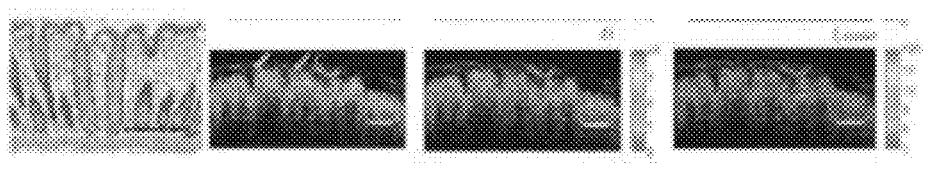

Since ISOCT can quantify tissue sub-diffractional structure properties, it can be used to enhance the OCT image contrast. As a demonstration, ex vivo human rectal colon biopsies were obtained and imaged by ISOCT (FIG. 14). Referring to FIG. 14b, the lateral OCT image averaged from a 60 μm layer of tissue is illustrated. The corresponding maps of D and $l_c$ are shown in FIGS. 14c and 14d, respectively. The pseudo-color maps are plotted in a HSV color space such that saturation and value are coded with the OCT intensity image while hue is presented with the value of D or $l_c$. The same approach is also demonstrated on cross-section views of OCT images as illustrated in FIGS. 14f and 14g. The surface of the tissue was detected and marked artificially so that the effect of inherent curvature can be eliminated and an analysis can be conducted in terms of the penetration depth with respect to the surface. With the color-coded image, the sub-diffractional physical properties can be co-registered with macroscopic tissue morphology.

Figure 9B:
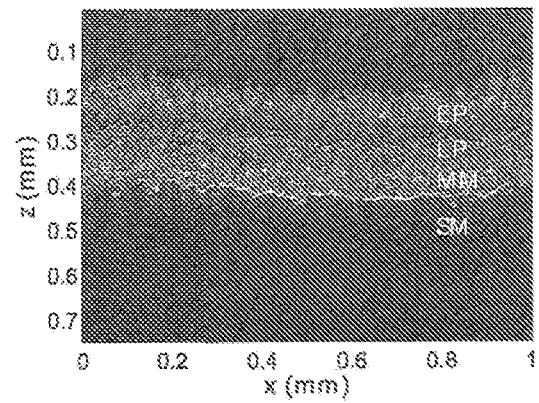
Figure 9C:
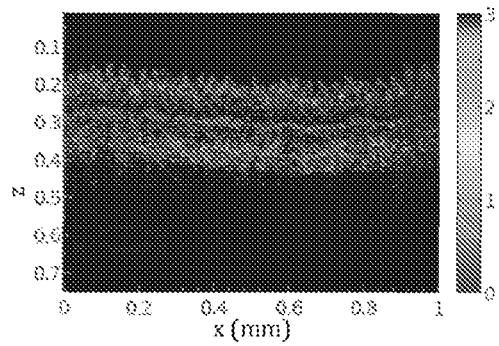

Ex vivo esophageal rat samples were obtained for ISOCT processing to further demonstrate the image contrast enhancement attributes of ISOCT (FIG. 9c). Various D values can be found from the different tissue types, such as epithelium, lamina propria, muscularis mucosa and sub-mucosa (FIG. 9c). These features can he realized during a real-time OCT acquisition and provide a sensitive contrast based on the subtle structural change which is beyond conventional OCT resolution.

Thus, a method for enhancing image contrast for a biological tissue is preferably accomplished in the following manner. One obtains image signal data for the biological tissue sample with spectroscopic optical coherence tomography with a calibrated instrument. As previously explained, one can obtain image signal data by actually performing an analysis of a biological tissue on site, for example with a bench-top, hand-held or fiber optic ISOCT instrumentation. Alternatively, one can be obtain image signal data by being provided such data from another who performed an analysis of a biological tissue at a remote site, for example with a bench-top, hand-held or fiber optic ISOCT instrumentation.

Once such image signal data is obtained, one processes the image signal data using one or more algorithms disclosed herein to obtain a plurality of D values. One then generates a Hue-Saturation-Value color space plot based upon the image signal data as a function of the plurality of D values. For example, one can obtain a plurality of D values by quantifying a tissue mass density correlation function with a length scale of sensitivity in sub-diffractional regime from the optical coherence tomography spectra for each three-dimensional voxel of spatial resolution.

The method can have broad utility for imaging a variety of biological tissue to achieve higher resolution and image contrast, such as detecting changes within at least one ultrastructural feature of the biological tissue due to onset of disease within the biological tissue. Examples where such features can be evident include biological tissues such as native tissues in biological organisms as well as clinical tissue samples suspected to contain atypical cells selected from the group consisting of early stage carcinogenic cells, pre-cancerous cells, dysfunctional cells, and cells infected or damaged by a viral agent, fungal agent, or bacterial agent.

The image contrast enhancement with ISOCT can be used to image, visualize-and/or quantify differences between two biological tissues of the same type, such as differences between normal tissues and tissues containing atypical cells. As used herein, "two closely related biological tissues" refers to the identical type of biological tissue that may differ in at least one physiological or metabolic property that distinguishes the two biological tissues. An example of at least one physiological or metabolic property is differential cellular gene product expression in a normal cell versus a precancerous cell or a cancerous cell. An additional example of at least one physiologic or metabolic property is microbial gene product expression attributed to infection by a microbial agent, such as a fungal agent, a bacterial agent, a viral agent or a combination of such microbial agents. An additional example of at least one physiologic or metabolic property is altered cellular gene product expression as a consequence of infection by a microbial agent, such as a fungal agent, a bacterial agent, a viral agent or a combination of such microbial agents.

Such differences between two biological tissues of the same type can be discerned by the ISOCT method in a number of representations. For example, one can obtain image signal data for a first biological tissue sample and a second biological tissue sample with spectroscopic optical coherence tomography with a calibrated instrument. Following obtaining image signal data, one can obtain a plurality of D values for the first biological tissue sample and the second biological tissue sample using the algorithms disclosed here. In one approach, one can quantify a tissue mass density correlation function with a length scale of sensitivity in sub-diffractional regime from the optical coherence tomography spectra for each three-dimensional voxel of spatial resolution the first biological tissue sample and the second biological tissue sample to obtain a plurality of D values for the first biological tissue sample and the second biological tissue sample. One can then generate a first Hue-Saturation-Value color space plot based upon the image signal data from the first biological tissue sample as a function or the plurality of D values for the first biological tissue sample. One can then generate a second Hue-Saturation-Value color space plot based upon the image signal data from the second biological tissue sample as a function of the plurality of D values for the second biological tissue sample. One then can generate a difference Hue-Saturation-Value color space plot from the first and second Hue-Saturation-Value color space plots, wherein the difference Hue-Saturation-Value color space plot represents an enhanced contrast image that reveals the atypical ultrastructure features of the second biological tissue.

Other representations of differences between two biological tissues of the same-type that can be discerned by the ISOCT method are feasible, such as pseudo-color plot presentations (for example, Hue-Saturation-Value color space plots), graphical representations of one or more properties from the full set of optical scattering properties, such as the anisotropic factor g, backscattering coefficient $\mu_b$, scattering coefficient $\mu_s$, or from tissue mass density correlation function derived properties, such as the D value, $I_c$ and $dn^2$. Such graphical representations can be presented as difference plots, for example.

The ISOCT method provides imaging solutions for minimizing invasiveness, reducing image processing time, lowering image costs, reducing radiation doses and/or optimizing resolution and/or contrast so that data can be more readily interpreted. The ISOCT method can have applications in medical imaging, ophthalmic applications, early diagnosis of cancer or diseases, cardiovascular applications, neurological applications, and/or dental applications.

EXAMPLES

Example 1. ISOCT Instrumentation, Calibration and Image Processing

ISOCT Instrumentation

A Fourier domain-OCT system with a supercontinuum source providing an illumination bandwidth from 650 to 800 nm was constructed for ISOCT (FIG. 7a). The axial resolution is ~1.5 μm, and the lateral resolution is ~10 μm with an effective NA 0.04. The scanning range is 2×2 mm on the lateral plane (x×y) and the B-scan rate is 10 fps. The spectra were first normalized by the reference spectrum and the OCT A-lines were normalized by the intensity profile of the focused beam. The OCT spectra were extracted by a short frequency Fourier 120 transform (SFFT) with a spectral resolution of 15 nm, relaxing the axial resolution to ~15 μm.

Referring to FIG. 7a, a low coherence laser beam output from a supercontinuum source (SuperK Versa, NKT photonics) was coupled into a single mode fiber, then collimated into an open space Michelson interferometer. A beam splitter (BS) split the beam into sample and reference arms. A well-corrected microscopic objective was used to create a 5 mW focused illumination with effective NA=0.04. A 2D galvo mirror (Galvo) was configured to steer the beam before the objective to realize the lateral scan. The specimen is placed on the sample stage (SS) during an imaging study. The reference arm included a reflecting mirror (M) and a quartz plate pair for dispersion compensation (DC). The reflected beams from two arms are recombined by the beam splitter and then coupled into another single mode fiber followed by a spectrometer. Inside the spectrometer, the interfered beam was collimated by an f=30 mm lens and directed to holographic diffraction grating (G) (1200 grooves/mm) to disperse the beam. A commercially-available lens (Nikon f=135 mm) was then used focused the dispersed beam on a 2048 pixel line scan camera (e2v) to record spectrum from 650 nm to 820 nm. Two function generators (Agilent) were synchronized to drive the galvo scanning mirror (FG2) and provide exposure trigger to the camera (FG1). A computer controlled the other galvo mirror through a DAQ (T1) card and collected the image signal from CCD camera via a frame grabber (Matrox). The current frame rate was set 10 fps to maximize the signal to noise ratio.

ISOCT Instrumentation Calibration

Figure 3A:
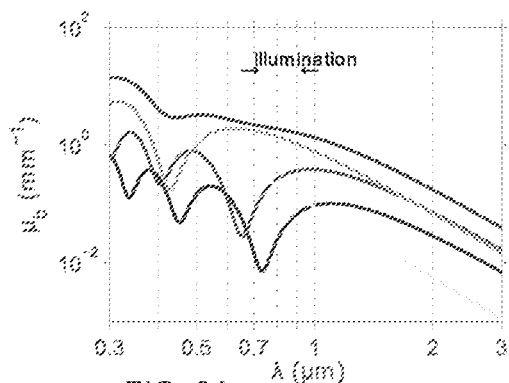
FIG. 3 depicts an exemplary phantom design (FIG. 3a) for a calibration of D value measurement; OCT spectra measured from 2 different D models (dotted line) (FIG. 3b); a calibration of the D value with a set of exemplary phantoms (FIG. 3c); D value axial resolution characterized with a two-layer phantom (FIG. 3d); and statistical robust analysis of D value measurement (FIG. 3e).
Figure 3B:
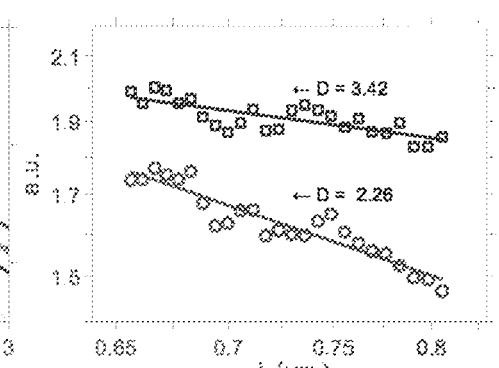
Figure 3C:
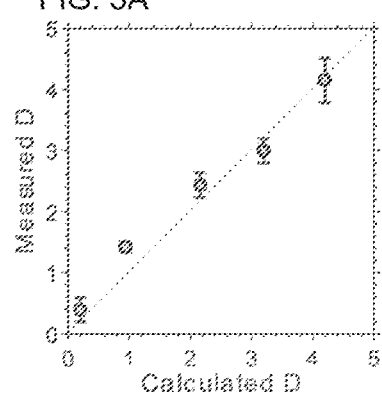
Figure 3D:
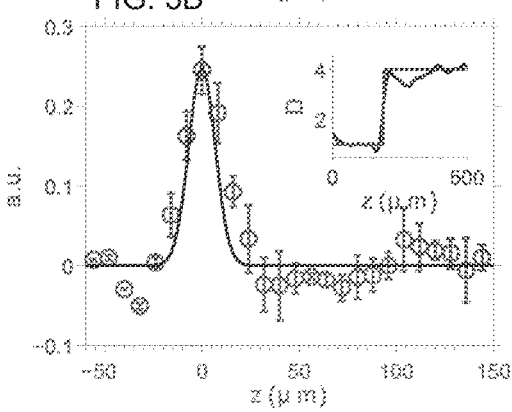

The following experiments were performed to calibrate the D value. An experimental phantom with a particular D value was prepared by mixing microspheres of different sizes in such a composition that the $\mu_b(k)$ follows the power law over the interrogated wavelength range. For the experimental phantom design, four types of polystyrene nanospheres with diameter of 360 nm, 300 nm, 200 nm and 80 nm in the concentration ratio of 6/20/60/150 (parts per nanosphere type, respectively) were prepared. Referring to FIG. 3a, individual $\mu_b$ terms from each nanosphere are presented in color (yellow-80 nm, green-200 nm, red-300 nm, blue-360 nm). FIG. 3b depicts OCT spectra measured from two different D models (dotted line), wherein one phantom had the composition 360 nm, 300 nm, 200 nm, 80 nm spheres in volume ratio of 6/20/60/150 and the other phantom had the same composition only without 80 nm spheres. Each spectrum was fitted with a power law to calculate the scattering power and D value (solid line). Based on the measured and designed D value, a system calibration was performed (FIG. 3c). The calibration of FIG. 3c showed that the system is able to measure D value with the precision of ±0.20 with 90% confidence using a linear regression on the calibration data. Due to the time-frequency analysis of SFFT, the axial resolution is sacrificed to gain the spectral information. Referring to FIG. 3d, a two-layer D phantom with solid agarose gel on the bottom and a solution on top was used to characterize the D value resolution. D measurement axial PSF calculated by taking derivative of the D value measurement curve from inset figure. Theoretical PSF in blue was determined by the Gaussian window used in SFFT analysis. The red step case function in the inset represent the designed D value discontinued at the layer boundary. The sample was a two-layer phantom with D=0.98, 4.12. Error bars represent the standard deviation across independent measurements.

In the practical scenario, the physical structure contributing to the OCT spectrum for each pixel in an image is deterministic and the variance exists among pixels. A robust statistical assessment may require a certain extent of averaging over a local volume, which should be large enough to represent the local optical properties yet small enough to pose spatial resolution.

Figure 3E:
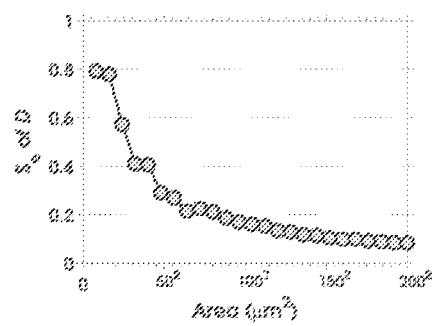

The following experiment was done to analyze the robustness of D value determination (FIG. 3e). A sample with 2% 80 nm polystyrene solution is imaged by ISOCT. An averaging square box is used on a 2D cross section OCT image to a select region of interest (ROI) in which D value of each voxel is calculated. The standard error of the D values inside ROI are plotted against the size of the averaging box area. To provide the local sensitivity of ±0.2, one can use a $60^2$ $\mu m^2$ area on an 2D OCT image or equivalent volume in 3D to estimate the local optical properties (FIG. 3e).

Referring to FIG. 4, the following experiment was performed to evaluate the effect on D value as a function of perturbation of the length scale of sensitivity of the model in the fractal regime. The original RI correlation function $C_n(\rho)$ was perturbed (FIG. 4a) in the following way: for the inner length scale $\rho_{min}$, the correlation function was truncated at $\rho_{min}$ so that $C_n'(\rho<\rho_{min})=C_n(\rho_{min})$. The curves represent function truncated at different $p_{min}$. Referring to FIG. 4b, the backscattering cross section per unit volume were calculated from data presented in FIG. 4a. FIG. 4c depicts the error of the calculated D valve. $\rho$ is the spatial displacement of the RI (mass density) correlation function.

Referring to FIG. 5, the following experiment was performed to evaluate the effect on D value by perturbation of the RI correlation function at upper length scales. For perturbation on the RI correlation function at the upper length scale $\rho_{max}$, the function is modified:

$$C_n^a(\rho) \times \frac{1}{\left(1 + \frac{\rho}{\rho_{max}}\right)^\gamma}. \tag{Eqn. 7}$$

When $\rho \ll \rho_{max}$, $C_n^a(\rho) = C_n(\rho)$; when $\rho > \rho_{max}$, the $C_n(\rho)$ decays in the power of 3 in the region $\rho_{max} < \rho < l_c$ from the original correlation function as if that there is no fluctuation in terms of mass density or RI beyond $\rho_{max}$. Referring to FIG. 5a, the curves represents function disturbed at different $\rho_{max}$. FIG. 5b presents the backscattering cross section per unit volume calculated, based upon data from FIG. 5a. FIG. 5c depicts the error of calculated D value.

ISOCT Data Processing Procedures

The spatially-resolved OCT spectrum is obtained by using SFFT on the 3D dataset. After normalization and averaging, the exponents of OCT spectrum is calculated by fitting with a power law with respect to k and D can be calculated using equation 2 or its simplified form equation 5. In parallel, the 3D OCT image is created and the $\mu_b$ and $\mu_s$ is quantified based on the image intensity and the intensity decay rate along the depth. The wave number k in Eqn. 6 or its original form $\mu_b/\mu_s$ from Eqn. 2, 3 is assigned to be the center value over the illumination bandwidth. By calculating the ratio of $\mu_b$ and $\mu_s$, $l_c$ is deduced. For an accurate measurement of D value and $\mu_b$ in deeper tissue, a correction is performed to compensate the attenuation when light propagates through tissue. The D value correction is calculated according to the wavelength dependent $\mu_s(k)$, which is obtained from the 4D dataset in a similar manner as calculating fps. The $\mu_b$ correction curve is an exponential function compensating the overall intensity decay.

Figure 8:
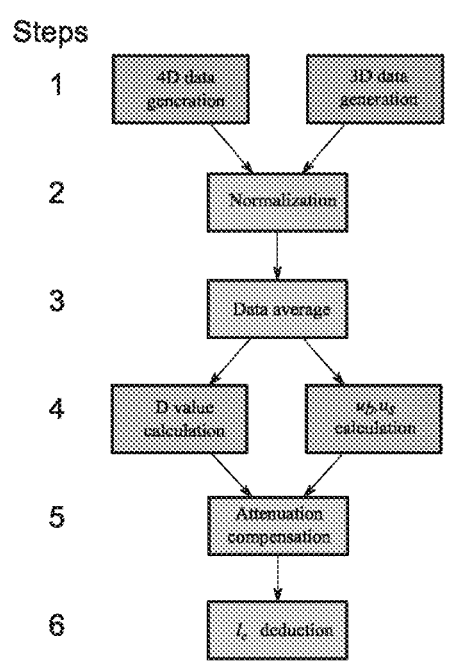
FIG. 8 illustrates a data processing procedure for ISOCT data analysis.

Referring to FIG. 8, the following steps are performed to process data from the ISOCT instrumentation.

Step 1: 3D and 4D data generation, 3D OCT image data was obtained by taking inverse Fourier transform on the interferometric signal after subtracting the DC component. SFFT was used to generate the 4D data with the spectral dimension in addition to the 3D spatial dimension. A Gaussian spectral wavelet window (FWHM=15 nm) filtered the interferometric data before the Fourier transform was taken. The wavelength dependent 3D data was generated when the wavelet window was scanned across the entire spectral range. Thus, each voxel had a corresponding spectrum.

Step 2: Data normalization. In order to eliminate the variance of the illumination condition, the raw interferometric data from the line scan camera was first normalized by the reflectance spectrum from the reference arm. The second normalization was crucial to get a accurate spectrum measurement. A normalization phantom was prepared with 2% 80 nm polystyrene spheres solution. The rationale of this phantom was that the backscattering coefficient can be controlled at the same level of tissue ~0.5 $mm^{-1}$, and the scattering power is well known to be $k^4$. The phantom was imaged and the spectrum from superficial 30 μm was extracted by SFFT as second spectral normalization.

Step 3: Data average. Averaging was performed on 3D and 4D data set at both the lateral plane and axial extents to yield robust results. The averaging volume was according to the curve in FIG. 3e. For example, the local sensitivity of ±0.2 is desired, one can use a $60^2$ μm² area on an 2D OCT image or equivalent volume in 3D. On the presented tissue data, a 50 μm×50 μm 2D window on the lateral plane and then a 50 μm window in the axial direction was applied for averaging. The total volume was $50^3$ μm³ so that the D value error less than 0.1 if a homogeneous medium were assumed.

Step 4: D value, $\mu_b$ and $\mu_s$ calculation. Equation 5 was used to calculate D value from each voxel when klc>>1, which is mostly the case in biological tissue. The exponent to the wave number of the square intensity of the OCT spectrum is equal to 4-D. Or one can use the original form Equation 2 for other klc values. Term $\mu_s$ was calculated based on Lambert-Beer's law that the intensity decays along depth due to the scattering attenuation. Term $\mu_b$ was calculated based on the absolute maximum intensity value according to Equation 1:

Although $\mu_b$ and $\mu_s$ are also wavelength dependent, their calculations are based on the 3D image data, and the values are regarded for the central wavelength for later calculation.

Step 5: Attenuation correction. As mentioned above, the wave attenuates as propagating through tissue and the attenuation is wavelength dependent which will introduce error in terms of the measurement on D and $\mu_b$ in the deeper tissue. Thus, the attenuation was compensated after the localized OCT spectrum was obtained:

$$\Pi(k,z)=\Pi'(k,z)\exp(-2b\mu_s(k)z) \quad \text{(Eqn. 8)},$$

where Π is the OCT spectrum obtained from SFFT and Π' is the scattering spectrum from a diffraction-limited volume without the error induced by the attenuation, which is represented by the exponential term. The term z is the penetration depth and k is the wave number. The equation can be deduced in log-log manner since the power law relationship of π(k,z) was already established. When approximations are made, $$\mu_s(k)=\beta \log(k)+c \quad \text{(Eqn. 9)},$$

and the above equation can be derived as the following equation:

$$\log(\Pi'(k,z))=\log(\Pi(k,z))+bz[\beta \log(k)+c] \quad \text{(Eqn. 10)}$$

The term bzβ represents the error introduced by the $\mu_s(k)$, and c is a constant. The wavelength dependent term $\mu_s(k)$ was calculated in the same manner as $\mu_s$ from the 4D data set, and the β was calculated using Eqn. 9. The compensation of $\mu_s(k)$ was done by adding depth dependent correction term bzβ to the calculated scattering power from the OCT spectrum Π(k,z). The accurate D value was then calculated by equation 5. The D value measurements were performed on a uniform phantom and the error of D value in terms of depth can be well corrected by the method described above.

The other correction methods are according to Eqn. 5 that $\mu_s$ is a power law function in terms of k with exponent equal to 1. Thus it can be directly plugged in Eqn. 8.

The compensation was performed to correct $\mu_b$ in a similar manner. An exponential function $\exp(2b\mu_s z)$ was multiplied on the intensity profile.

Step 6: Term $dn^2$, $l_c$ deduction. Eqn. 6 was used to calculate $l_c$ after substituting D, α ($\mu_b/\mu_s$) was quantified at Steps 4 and 5. Eqn. 2 and 4 was used to calculate $N_c$ and $dn^2$.

Example 2. ISOCT Imaging of Rat Esophageal Tissue Ex Vivo.

Fresh rat-esophagus was dissected and imaged as illustrated in FIG. 9. The tissue histology revealed a stratified tissue structure having epithelium (EP), laminar propria (LP), muscularis mucosa (MM) and submucosa (SM), with the layer boundaries marked artificially to separate the different layers (FIG. 9a; the bar inset is a 100 μm length standard). An area of 3000 μm² (300 μm×10 μm in x-z) was used for averaging area to smooth the wavelength dependent image at each SFFT to obtain localized D value.

Figure 9D:
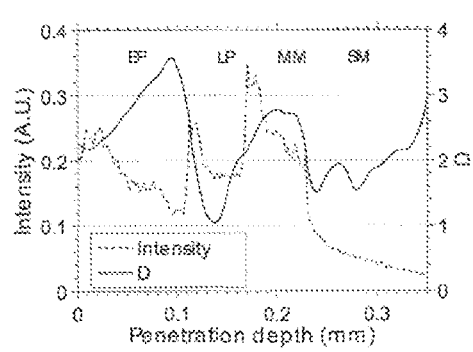

The original OCT linear intensity map plot for this sample in gray scale is illustrated in FIG. 9b. A pseudo-color image in Hue-Saturation-Value (HSV) color space was created to visualize D value, as illustrated in FIG. 9c. The value and saturation can be encoded by the intensity map of the original OCT and the hue was encoded by the D value as a color bar illustrates (FIG. 9c). Average D values are compared with image intensity in terms of uniform penetration depth, and the D distribution from different layers can be appreciated (FIG. 9d).

Example 3. ISOCT Imaging of Human Colon Tissue.

Human rectal colon ex vivo biopsy samples were obtained by the protocol approved by the IACUC committee board in North Shore University Health Systems. Immediately after removal, the specimens were kept in phosphate buffered saline (PBS) solution and refrigerated. The entire measurement was completed within 4 hours of dissection. Standard protocols for histology preparation were used. The specimens were fixed in 10% formalin immediately after measurement, embedded in paraffin wax and cut into 4 μm thick sections. Histology staining was performed using hematoxylin and eosin. Samples were visualized using an Olympus BH2 bright field microscope with 10× magnification and images were taken using a SPOT camera.

The tissue mass density correlation function and the optical properties of the human colon tissue biopsy was analyzed in terms of penetration depth given the topography map as illustrated for the rat esophageal tissue ex vivo sample of Example 2. The surface of the human colon tissue sample was artificially aligned to be flat so that the effect of complex curvature was eliminated. FIGS. 10a and 10b show the 3D image of human colon co-registered with anisotropic factor g and D value. The scale of the image was 2×2×1 mm. FIGS. 10c, 10d and 10e illustrate tissue mass density correlation function parameters in terms of the physical properties. D value, $l_c$ and $dn^2$, respectively, FIGS. 10f, 10g and 10h illustrate the full optical properties (g, $\mu_s'$ and $\mu_b$) in terms of penetration depth.

Example 4. ISOCT Imaging Early Stage Colon Carcinoma

To demonstrate the significance of quantifying the sub-diffractional RI correlation function of intact tissue, the ISOCT imaging method was applied to detect the field effect of colon carcinogenesis. The field effect states that the formation of a tumor is a consequence of a chronic condition on the entire organ, rather than a sudden and isolated event. During early carcinogenesis, subtle structural changes can arise that are detectable at locations apart from the eventual site of tumorigenesis. The field effect thus provides means to detect cancer at an early stage via an easily accessible portion of the organ. Based on this principle, ISOCT imaging studies were performed to detect the colonic cancer field effect. The ex vivo colon biopsies were obtained from the patients going through colonoscopy screening. While the colonic polyp, which is pre-malignant tissue growth on the lining of the colon, can be found anywhere on the entire colon, the biopsies were taken only from rectal portion. A patient is categorized as having advanced adenoma (AA) if (s)he possesses at least one polyp larger than 9 mm in diameter, since AA patients have the highest risk of developing colon cancer. The control samples are taken from patients free of polyps. The sample pool included a total of 10 control and 13 AA patients for data analysis.

In order to study the origin of the structural change in early colon cancer development, the LP and the cryptal areas were isolated by image processing on the 3D OCT morphology, and the RI correlation functional forms were quantified respectively. In general, the value of D was higher in AA tissue than control tissue (FIG. 11). The most significant differences occurred around ~100 µm inside the crypts and after ~200 µm deep in lamina propria. Also, $l_c$ in AA tissue was larger than control tissue in both the LP and cryptal area (FIG. 12). On the other hand, the conventional optical properties, $\mu_b$ and $\mu_s$, used historically did not yield significant differences between AA tissue and control tissue (FIG. 13). By measuring the sub-diffractional RI correlation function, ISOCT imaging method detected early carcinogenesis owing to its high sensitivity.

Terminology and Definitions

The terminology used herein is for the purpose of describing particular embodiments only, and is not intended to be limiting. With respect to the use of substantially, any plural and/or singular terms herein, those having skill in the art can translate from the plural as is appropriate to the context and/or application. The various singular/plural permutations may be expressly set forth herein for the sake of clarity.

Terms used herein are intended as "open" terms (e.g., the term "including" should be interpreted as "including but not limited to," the term "having" should he interpreted as "having at least," the term "includes" should be interpreted as "includes but is not limited to," etc.).

Furthermore, in those instances where a convention analogous to "at least one of A,B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or; B or "A and B."

All language such as "up to," "at least," "greater than," "less than," and the like, include the number recited and refer to ranges which can subsequently be broken down into subranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

As used herein, a "pseudo-color plot" refers to any color-based or color-scalable plot to depict changes in a graphical representation. Examples of a pseudo-color plot, include a Hue-Saturation-Value color space plot.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiments or examples disclosed, but that the present invention will include all embodiments filling within the scope of the appended claims.

What is claimed is:

1. A method comprising:
   generating, using an inverse spectroscopic optical coherence tomography (ISOCT) apparatus, three-dimensional (3D) data using an inverse Fourier transform of interferometric data related to a tissue sample;
   generating, using the ISOCT apparatus, four-dimensional (4D) data using a short frequency Fourier transform of the interferometric data;
   calculating, using an ISOCT apparatus, a mass fractal dimension value of the tissue sample based on the 4D data;
   calculating, using an ISOCT apparatus, a backscattering coefficient of the tissue sample based on the 3D data;
   calculating, using an ISOCT apparatus, a scattering coefficient of the tissue sample based on the 3D data and 4D data; and
   determining, using an ISOCT apparatus, a type of tissue based on at least one of the mass fractal dimension value, the backscattering coefficient, and the scattering coefficient of the tissue sample.

2. The method as defined in claim 1, further including correcting at least one of the mass fractal dimension value, the backscattering coefficient, and the scattering coefficient based on a wavelength attenuation.

3. The method as defined in claim 1, further including reducing at least one of the mass fractal dimension value, the backscattering coefficient, and the scattering coefficient based on an upper length scale of a correlation function.

4. The method as defined in claim 1, further including filtering the interferometric data using a Gaussian spectral wavelet window.

5. The method as defined in claim 1, further including averaging the 3D data and the 4D data at both the lateral plane and axial extents to yield robust results.

6. The method as defined in claim 1, wherein the mass fractal dimension value is calculated based for each voxel.

7. The method as defined in claim 1, further including normalizing the 3D data and the 4D data using a reflectance spectrum from a reference arm.

8. The method as defined in claim 1, wherein the backscattering coefficient is calculated based on an absolute minimum intensity value.

9. The method as defined in claim 1, further including selecting a region of interest for which to calculate the mass fractal dimension value of the tissue sample.

10. An apparatus comprising:
a computer connected to a laser source, an interferometer, and a charge coupled device camera, the computer to control the interferometer and the camera to form an inverse spectroscopic optical coherence tomography (ISOCT) system, the computer having a processor to:
generate three-dimensional (3D) data using an inverse Fourier transform of interferometric data created by the interferometer and collected by the charge coupled device camera related to a tissue sample;
generate four-dimensional (4D) data using a short frequency Fourier transform of the interferometric created by the interferometer and collected by the charge coupled device camera data;
calculate a mass fractal dimension value of the tissue sample based on the 4D data;
calculate a backscattering coefficient of the tissue sample based on the 3D data;
calculate a scattering coefficient of the tissue sample based on the 3D data and 4D data; and
determine a type of tissue based on at least one of the mass fractal dimension value, the backscattering coefficient, and the scattering coefficient of the tissue sample.

11. The apparatus as defined in claim 10, further including a sample stage on which a specimen is placed.

12. The apparatus as defined in claim 10, further including a fiber optic based probe to analyze internal biological tissues in vivo.

13. The apparatus as defined in claim 10, further including a scanning mechanism on a piezoelectric plate to keep a size of a probe less than 1 nanometer.

14. The apparatus as defined in claim 10, further including a gradient-index lens to focus light from the fiber and collect backscattered light.

15. A non-transitory computer readable storage medium including instructions that, when executed, causes a processor configured as part of an inverse spectroscopic optical coherence tomography (ISOCT) system to at least:
generate three-dimensional (3D) data using an inverse Fourier transform of interferometric data related to a tissue sample;
generate four-dimensional (4D) data using a short frequency Fourier transform of the interferometric data;
calculate a mass fractal dimension value of the tissue sample based on the 4D data;
calculate a backscattering coefficient of the tissue sample based on the 3D data;
calculate a scattering coefficient of the tissue sample based on the 3D data and the 4D data; and
determine a type of tissue based on at least one of the mass fractal dimension value, the backscattering coefficient, and the scattering coefficient of the tissue sample.

16. The storage medium of claim 15, wherein the instructions, when executed, further cause the processor to correct at least one of the mass fractal dimension value, the backscattering coefficient, and the scattering coefficient based on a wavelength attenuation.

17. The storage medium of claim 15, wherein the instructions, when executed, further cause the processor to reduce at least one of the mass fractal dimension value, the backscattering coefficient, and the scattering coefficient based on an upper length scale of a correlation function.

18. The storage medium of claim 15, wherein the instructions, when executed, further cause the processor to filter the interferometric data using a Gaussian spectral wavelet window.

19. The storage medium of claim 15, wherein the instructions, when executed, further cause the processor to select a region of interest for which to calculate the mass fractal dimension value of the tissue sample.

20. The storage medium of claim 15, wherein the instructions, when executed, further cause the processor to normalize the 3D data and the 4D data using a reflectance spectrum from a reference arm.

* * * * *